United States Patent [19]
Bare

[11] Patent Number: 5,098,925
[45] Date of Patent: Mar. 24, 1992

[54] SPIRO-DIHYDROISOINDOLE COMPOUNDS

[75] Inventor: Thomas M. Bare, West Chester, Pa.

[73] Assignee: ICI Americas Inc., Wilmington, Del.

[21] Appl. No.: 650,503

[22] Filed: Feb. 5, 1991

[30] Foreign Application Priority Data

Feb. 8, 1990 [GB] United Kingdom ................ 9002834

[51] Int. Cl.$^5$ .................... C07D 209/96; A61K 31/40
[52] U.S. Cl. ..................................... 514/409; 548/411
[58] Field of Search ......................... 548/411; 514/409

[56] References Cited

U.S. PATENT DOCUMENTS 3,308,134  3/1967  Plostnieks ........................... 548/411
4,240,963 12/1980  Laas et al. ........................... 548/411

OTHER PUBLICATIONS

Robinson et al., "A Novel Rearrangement Forming . . .", Tetrahedron Letters vol. 30, No. 39, pp. 5203-5206 (1989).

*Primary Examiner*—Joseph Paul Brust
*Assistant Examiner*—M. S. H. Gabilan
*Attorney, Agent, or Firm*—James T. Jones

[57] ABSTRACT

The present invention relates to spiroisoindolines that are antagonists at the phencyclidine receptor of the N-methyl-D-aspartate receptor complex and which are useful when such antagonism is desired such as in the treatment of neurological disorders. The invention further provides processes for preparing the spiroisoindolines, intermediates useful for their synthesis, pharmaceutical compositions containing them, and methods for their use.

21 Claims, No Drawings

SPIRO-DIHYDROISOINDOLE COMPOUNDS

This invention relates to spiroisoindoline compounds useful in the treatment of neurological disorders generally in mammals such as man. More specifically, the compounds are useful in the treatment of strokes and/or other neurodegenerative disorders such as hypoglycemia, cerebral palsy, transient cerebral ischemic attack, perinatal asphyxia, epilepsy, Huntington's chorea, Alzheimer's disease, Olivo-pontocerebellar atrophy, anoxia such as from drowning, and spinal cord injury. The invention particularly relates to novel spiroisoindoline compounds useful in reducing neurological degeneration such as can be induced by a stroke and the associated functional impairment which can result. Treatment using a compound of the invention can be remedial or therapeutic as by administering a compound following an ischemic event to mitigate the effects of that event. Treatment can also be prophylactic or prospective by administering a compound in anticipation that an ischemic event may occur, for example in a patient who is prone to stroke.

It is known that ischemic events can trigger a dramatic increase in extracellular concentrations of the excitatory amino acids glutamate and aspartate which can, in turn, cause prolonged neuronal excitation leading to a massive influx of calcium from extracellular to intracellular sites in brain neural cells. A calcium overload can thereby by created which leads to a cascade of events leading to cell catabolism and eventually resulting in cell death.

The N-Methyl-D-Aspartate (NMDA) receptor complex is believed to play a significant role in the cascade of events leading to cell necrosis following an ischemic event. It has been observed that several NMDA antagonists demonstrate a neuroprotective action in several animal models of stroke even when administered as long as 24 hours after an ischemica event, i.e. there appears to be a window of opportunity for therapeutic intervention after the occurrence of stroke. The compounds provided by the invention are antagonists at the phencyclidine (PCP) receptor of the NMDA receptor complex and may be useful in the treatment of neurodegenerative conditions which result following a stroke. The compounds may also be useful whenever it is desired to provide thereby involving the administration of PCP receptor antagonists, for examples when it is desired to combat neurodegenerative disorders other than stroke such as those noted above.

According to the invention there is provided a pharmaceutical composition suitable for the treatment of neurological disorders, comprising a compound of formula I (formula set out, together with other formulae referred to by Roman numerals, on pages following the Examples), or a pharmaceutically acceptable salt thereof, wherein:

R is selected from a group consisting of hydrogen, benzyl, and (1-5C)alkyl optionally containing a double or triple bond provided that, if a double or triple bond is present, at least one methylene group intervenes between said double or triple bond and the nitrogen atom to which said alkyl is attached, $Y^1$, $Y^2$, $Y^3$ and $Y^4$ are independently selected from a group consisting of hydrogen, hydroxy, halo, (1-5C)alkyl, (1-5C)alkoxy, and trifluoromethyl, provided that not more than two of $Y^1$, $Y^2$, $Y^3$ and $Y^4$ are other than hydrogen, ring A is selected from the group consisting of the members shown as formulae Ia, Ib, Ic, and Id wherein in said formulae, X is selected from a group consisting of O, S and N-$R^1$, wherein $R^1$ has the meaning given above for R, and $Z^1$, $Z^2$, $Z^3$ and $Z^4$ are independently selected from hydrogen, hydroxy, halo, (1-5 C) alkyl, (1-5 C) alkoxy, and trifluoromethyl, provided that not more than two of $Z^1$, $Z^2$, $Z^3$ and $Z^4$ are other than hydrogen, and n is 1, 2, 3, or 4;

and a pharmaceutically acceptable diluent or carrier.

The invention further provides a method for the treatment of neurological disorders, comprising administering to a mammal in need of such treatment an effective amount of a compound of formula I as defined above, or a pharmaceutically acceptable salt thereof.

The compound spiro[indan-1,1'-(1,3-dihydroisoindole)] is known, for example for Tetrahedron. Lett., 30(39), 5203-5206, (1989). The remaining compounds within the scope of formula I as defined above are believed to be novel, however, and are provided as an additional feature of the invention. The novel compounds thus include those of formula I as defined above provided that, when each of $Y^1$-$Y^4$ is H, ring A is of formula Ia, each of $Z^1$-$Z^4$ is H, and n=1, R is not H.

It will be appreciated that compounds of formula I contain as asymmetrically substituted carbon atom, and accordingly may exist in, and be isolated in, optically-active and racemic forms. In addition, it will be appreciated that certain compounds of formula I, for example, those containing a double bond, may exist in, and be isolated in, separate stereoisomeric forms ('E' and 'Z') about that group. Some compounds may exist in more than one tautomeric form. Some compounds may exhibit polymorphism. It is to be understood that the present invention encompasses any racemic, optically-active, polymorphic or stereoisomeric form, or mixtures thereof, which form possesses properties useful in the treatment of neurodegenerative disorders, it being well known in the art how to prepared optically-active forms (for example, by resolution of the racemic form or by synthesis from optically-active starting materials) and individual 'E' and 'Z' stereoisomers (for example, by chromatographic separation of a mixture thereof) and how to determine neuroprotective properties by the standard tests described hereinafter.

In this specification the terms "alkyl", and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

"Halo" as used generally herein means fluoro, chloro, bromo, or iodo.

Particular values of R as (1-5 C) alkyl include methyl, ethyl, propyl, isopropyl, butyl, sec-butyl, t-butyl, isobutyl, pentyl, and isopentyl; and, when R contains an optional double or triple bond, particular values include allyl and propargyl.

Particular values of $Y^1$, $Y^2$, $Y^3$ and $Y^4$ as halo include fluoro and chloro.

Particular values of $Y^1$, $Y^2$, $Y^3$ and $Y^4$ as (1-5 C) alkyl include methyl, ethyl, propyl, isopropyl, butyl, sec-butyl, t-butyl, isobutyl, pentyl and isopentyl.

Particular values of $Y^1$, $Y^2$, $Y^3$ and $Y^4$ as (1-5 C) alkoxy include methoxy, ethoxy, propoxy, isopropoxy, butoxy sec-butoxy, isobutoxy, t-butoxy, pentoxy and isopentoxy.

Particular values of $Z^1$, $Z^2$, $Z^3$, and $Z^4$ and halo include fluoro and chloro.

Particular values of $Z^1$, $Z^2$, $Z^3$ and $Z^4$ and (1-5 C) alkyl include methyl, ethyl, propyl, isopropyl, butyl, sec-butyl, t-butyl, isobutyl, pentyl and isopentyl.

Particular values of $Z^1$, $Z^2$, $Z^3$ and $Z^4$ as (1-5 C) alkoxy include methoxy, ethoxy, propoxy, isopropoxy, butoxy, sec-butoxy, isobutoxy, t-butoxy, pentoxy and isopentoxy.

Particular values of $R^1$ when X is N-$R^1$ include (1-5 C) alkyl, (1-5 C) alkyl having the same particular values as those given for $Y^1$-$Y^4$ above.

More particular values of R include hydrogen, methyl, ethyl, propyl, and butyl.

More particular values of $Y^1$, $Y^2$, $Y^3$ and $Y^4$ include hydrogen, hydroxy, methyl, ethyl, propyl, methoxy, ethoxy, and propoxy.

More particular values of $Z^1$, $Z^2$, $Z^3$, and $Z^4$ include hydrogen, hydroxy, methyl, ethyl, propyl, methoxy, ethoxy, and propoxy.

More particular values of X include O, S, N-methyl, N-ethyl, and N-propyl.

More particular values of n are 1, 2 and 3.

Typical values of R include hydrogen, methyl, ethyl and propyl.

Typical values of $Y^1$, $Y^2$, $Y^3$ and $Y^4$ include hydrogen, hydroxy, methoxy, and ethoxy.

Typical values of $Z^1$, $Z^2$, $Z^3$, and $Z^4$ include hydrogen, hydroxy, methoxy, and ethoxy.

Typical values of X include S. It will be appreciated that within the above definitions there are included a number of subgroups of compounds, for example, (a) compounds of formula Ia
(b) compounds of formula If
(c) compounds of formula Ig
(d) compounds of formula Ih In the formulae (Ie)-(Ih), R, n, $Z^1$-$Z^4$, and $Y^1$-$Y^4$ are as previously defined. The above subgroups of compounds include the pharmaceutically acceptable addition salts thereof. Spiroisoindolines of formula I can be made by processes which include processes known in the chemical arts for the production of structurally analogous compounds. Such processes for the manufacture of a spiroisoindoline of formula I as defined above are provided as further features of the invention and are illustrated by the following procedures in which the meanings of generic radicals are as given above unless otherwise qualified. The processes can be effected, generally:

(a) for a compound of formula I wherein R is hydrogen, by reducing a spirolactam of formula II. The reduction can be effected with with a suitable reducing agent, in the presence of a suitable solvent or diluent, and (generally) at a temperature of 30° to 120° C. For example, a spirolactam of formula II can be suspended in a diluent such as tetrahydrofuran and refluxed with a reducing agent such as lithium aluminum hydride to yield the corresponding spiroisoindoline of formula I wherein R is hydrogen.

(b) for a compound of formula I wherein R is (1-5 C) alkyl optionally containing a double or triple bond, by alkylating a spiroisoindoline of formula I wherein R is hydrogen with an appropriate alkylating agent. Suitable alkylating agents include (saturated or unsaturated) alkyl halides (including the iodide, bromide, and chloride). If the methyl (R=$CH_3$) spiroisoindoline is desired, it is preferred to reductively methylate the corresponding (R=H) spiroisoindoline via the Eschweiler-Clarke reaction by employing a mixture of formaldehyde and formic acid.

(c) for a compound of formula I wherein any of $Y^1$-$Y^4$ and/or $Z^1$-$Z^4$ is hydroxy, by reacting a spiroisoindoline of formula I, wherein the corresponding value(s) of $Y^1$-$Y^4$ and/or $Z^1$-$Z^4$ is alkoxy, with an agent suitable for cleaving aryl alkyl ethers, e.g. a boron trihalide such as boron trichloride or boron tribromode to cleave the said alkoxy value(s) to hydroxy.

If not commercially available, the necessary starting materials for the above procedures may be made by procedures which are selected from standard organic chemical techniques, techniques which are analogous to the synthesis of known, structurally similar compounds, or techniques which are analogous to the above described procedures or the procedures described in the examples.

A spirolactam of formula II can be obtained by first reacting a corresponding spirolactone of formula III with excess ammonium hydroxide or, preferably, a combination of excess ammonium hydroxide and ammonium chloride under pressure (about 35 to about 100 bar) and within a temperature range of 200° to 280° C. The reaction product will generally contain, in addition to other products, the desired spirolactam of formula II plus an olefin amide by-product having the structure shown as formula IV. The compounds of formulae II and IV can be separated from any other reaction products (e.g. by chromatography) as a mixture and then reacted with trifluoroacetic acid to convert said olefin amide of formula IV to the desired spirolactam of formula II.

A spirolactam of formula II can also be obtained by treating a spirolactone of formula III with methylaluminum chloroamide (which can be made by reacting anhydrous ammonium chloride with trimethylalumium) in a suitable organic solvent. In general, a mixture is produced containing compounds having formulae IV and V. The mixture can be treated with trifluoroacetic acid to yield the desired spirolactam of formula II.

A spirolactone of formula III can be obtained by reacting a dilithiated N-methylbenzamide of formula VI with a ketone of formula VII in the presence of a solvent or diluent such as tetrahydrofuran and, generally, under an inert atmosphere. A dilithiated benzamide of formula VI can be made by reacting a N-methylbenzamide of formula VIII with an alkyllithium compound, for example n-butyllithium by processes well known in the art. See, for example, W. H. Puterbaugh and C. R. Hauser, J. Org. Chem., 29, 853 (1964).

If hydroxy functionality is desired in a final compound of formula I at any of the positions $Y^1$-$Y^4$ or $Z^1$-$Z^4$, it may be advantageous to protect any hydroxy functionality which has been incorporated into any intermediate or precursor at $Y^1$-$Y^4$ or $Z^1$-$Z^4$ prior to reducing a lactam of formula II to a corresponding spiroamine of formula I in order to facilitate the reduction and workup. Such protection can be afforded by converting the hydroxy group(s) to alkxoy group(s) such as methoxy group(s). However, if an alkoxy moiety is present in the molecular prior to converting a spirolactone of formula III to a spirolactam of formula II by reacting the former with an ammonium hydroxide/ammonium chloride combination, the alkoxy group may be cleaved to hydroxy. It may thus be necessary for reduction to occur smoothly to re-protect the hydroxy functionality by converting it back to alkoxy (e.g. methoxy) as by reacting the lactam with an alkyl halide, for example methyl iodide, before reducing the lactam to the spiroamine. If hydroxy functionality is desired in the final spiroisoindoline product, the alkoxy moiety can be recleaved, for example by reacting the (alkoxy) spiroisoindoline with an agent suitable for cleaving aryl alkyl ethers, e.g. a boron trihalide such as boron tribromide or boron trichloride, Similarly, when reacting a dilithiated N-methylbenzamide of formula VI with a ketone of formula VII to form a spirolactone of formula III, no hydroxy functionality should be present for $Y^1$–$Y^4$ or $Z^1$–$Z^4$ to avoid quenching the reaction. The hydroxy functionality can be introduced following reduction of the spirolactam of formula II as described above.

Examples of suitable pharmaceutically acceptable salts are organic acid addition salts formed with acids with form a physiologically acceptable anion, for example, tosylate, methanesulfonate, acetate, tartrate, citrate, succinate, benzoate, ascorbate, a-ketoglutarate, and a-glycerophosphate. Suitable inorganic salts may also be formed such as sulfate, nitrate, and hydrochloride. Pharmaceutically acceptable salts may be obtained using standard procedures well known in the art, for example by reacting a spiroisoindoline of formula I with a suitable acid affording a physiologically acceptable anion.

When used to intervene therapeutically following a stroke, a spiroisoindoline of formula I is generally administered as an appropriate pharmaceutical composition which comprises a spiroisoindoline of formula I as defined hereinbefore together with a pharmaceutically acceptable diluent or carrier, the composition being adapted for the particular route of administration chosen. Such compositions are provided as a further feature of the invention. They may be obtained employing conventional procedure and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection or infusion; in the form of aerosols or nebuliser solutions or suspensions for administration by inhalation; and in the form of powders together with pharmaceutically acceptable inert solid diluents such as lactose for administration by insufflation.

The dose of compound of formula I which is administered will necessarily be varied according to principles well known in the art taking account of the route of administration, the severity of the post-ischemic disorder, and the size and age of the patient. In general, a compound of formula I will be administered to a warm blooded animal (such as man) so that an effective dose is received, for example a dose in the range of about 0.02 to about 50 mg/kg body weight.

It will be apparent to those skilled in the art that a compound of formula I can be co-administered with other therapeutic or prophylactic agents and/or medicaments that are not medically incompatible therewith.

The actions of compounds of formula I as an antagonist at the phencyclidine (PCP) receptor of the NMDA receptor complex can be shown using known in vitro tests, for example that described in Vignon et al., Brain Research, 280, 194–197 (1983). Vignon et al. disclose that tritiated N-(1-[2-thienyl]cyclohexyl)-3,4-[$^3$H]-piperidine (also abbreviated as [$^3$H]-TCP) binds to PCP binding sites (e.g. in rat brains) more strongly than PCP itself. It is known that, by binding to the PCP site, transmembrane calcium channels are effectively blocked such that calcium overload leading to cell death is mitigated or prevented. [$^3$H]-TCP thus provides a useful tool for measuring the binding affinities of compounds which bind to PCP receptors such as the PCP site in the NMDA receptor complex. It is known that PCP and TCP block and NMDA receptor-operated calcium channel and hence that, by using [$^3$H]-TCP as a standard to probe the binding affinity of compounds which mimic the action of PCP, their potential as calcium channel blocking agents and, accordingly, their potential as therapeutic agents following a stroke, can be measured.

Specifically when it is desired to measure the binding affinity of a compound of formula I, a source of (brain) NMDA receptors is generated by preparing neuronal synaptic membranes from adult Sprague-Dawley rats. In brief, freshly dissected cortices and hippocampi were homogenized in 0.32 M sucrose (100 mg/ml). Synaptosomes are isolated by centrifugation (1000 ×g, 10 min), pelleted (20000×g, 20 min) and resuspended. The suspension is centrifuged for 20 minutes at 8000×g; the resulting supernatant and buffy coat were washed twice (4800×g, 10 min.). The final pellet is quickly frozen (Dry Ice -ethanol bath) under double deionized water and stored at −70° C.

The procedure for [$^3$H]-TCP binding is adapted from Vignon et al. (1983). The day of the experiment thawed membranes are homogenized in buffer (5 mM tris(hydroxymethyl)amiomethane hydrochloride, pH 7.7, available from Sigma), with a tissue homogenizer (POLYTRON%, available from Brinkman) incubated for 20 minutes at 37° C. and washed twice by centrifugation. [$^3$H]-TCP (2.5 nM) and test compounds are incubated with membranes for 30 minutes at 37° C. Nonspecific binding is determined with 100 µM MK-801, a calcium channel blocking agent well known and characterized in the art as set forth for example, in European Patent Application 0 230 370, published July 29, 1987. The reaction is terminated by vacuum filtration, over glass fiber filters, on a Brandel cell harvester, Filters, presoaked in 0.2% polyethylenimine, are rinsed 3 times with 3 ml ice cold buffer. Radioactivity is measured by liquid scintillation counting. The specific activity of the [$^3$H]TCP is used to convert the radioactivity measured to concentration [$^3$H]TCP bound. The specific binding is obtained by subtracting the nonspecific binding, that remaining in the presence of 100 µM MK-801. Logit-log plots of displacement of specific [$^3$H]TCP binding against test compound concentration are fit with least squares linear regression. IC50 values, the best fit estimate of the concentration of test compound which results in 50% inhibition of total specific [$^3$H]TCP binding, reflect binding affinity. Typical IC50 values for compounds according to the invention are generally less than 20 µM. For example, the IC50 value for the compound of Example 18 was 5.0 µM, and the IC50 value for the compound of Example 20 was 0.6 µM.

It will be understood that the useful biological properties of compounds of the invention may also be demonstrated, for example, in laboratory animals such as rat, gerbils and cats. Typically an animal is rendered ischemic, for example, for transient occlusion of the carotid artery. A test compound is then administered to said ischemic animal at or about the time of the ischemica event. The ability of the test compound to reduce or prevent neurological degeneration may then be assessed, for example, by sacrificing the animal, followed by conventional histological examination of suitable brain tissue. For example, the following is a description of a suitable test in vivo using the gerbil model.

When testing in vivo using the gerbil ischemic model, adult female Mongolian gerbils (50-70 g) are anesthetized with 2 to 3% halothane. The bilateral common carotid arteries at the neck are exposed and occluded with microaneurysm clips. After 10 min (unless specified), the clips are removed and the blood flow through the carotid arteries is restored and the skin is sutured. Test compounds are administered intraperitoneally both pre- and post-occlusion, for example 45 minutes before and 5 minutes after occlusion of the carotid arteries. Sham-operated animals are treated in the same manner except that the arteries are not clamped. Gross behavioral observations along with motor activity are recorded for 2 hr on the first (24 hr) day following the occlusion. After 4 days, objects are sacrificed (decapitation), brains are removed, fixed, sections and stained with hematoxylin/eosin and cresyl violet.

The brain sections are rated for neuronal damage in the hippocampus using the following rating scale;
0 = undamaged, normal
1 = slight damage (up to 25%)—restricted CA1/-subiculum border
2 = moderate damage (up to 50%)—obvious damage, restricted to less than half of CA1 field
3 = marked damage (up to 75%)—involving greater than half of CA1 field
4 = damage extending beyond CA1 field Sections (7 micron) are evaluated from each brain. Occasionally, asymmetrical damage may be noted and the rating assigned is the average score of the two sides. The average brain damage rating score for each group is recorded, and the damage scores of the drug treated group are compared to the vehicle-treated group using Wilcoxcon ranks sum test.

In general, compounds of the invention show activity in the above in vivo test at a dose of 80 mg/kg intraperitoneal (ip) or less without any overt toxic effects. By way of illustration, the compound described hereinafter in Example 21 produced a significant neuroprotective effect following an ip does of 60 mg/kg without any overt toxic effects.

The invention will now be illustrated by the following non-limiting examples in which, unless stated otherwise;

(i) temperatures are given in degrees Celsius (C); operations were carried out at room or ambient temperature, that is, at a temperature in the range of 18°-25°;

(ii) evaporation of solvent was carried out using a rotary evaporator under reduced pressure (600-4000 pascals; 4.5-30 mm Hg) with a bath temperature of up to 60°;

(iii) flash chromatography was carried out on Merck Kieselgel (Art 9385) and column chromatography on Merck Kieselgel 60 (Art 7734); [these materials were obtained from E. Merck, Darmstadt, W. Germany]; thin layer chromatography (TLC) was carried out on Analtech 0.25 mm silica gel GHLF plates (Art 21521), obtainable from Analtech, Newark, DE, USA;

(iv) in general, the course of reactions was followed by TLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) all final products were essentially pure by TLC and had satisfactory nuclear magnetic resonance (NMR) spectra and microanalytical data;

(vii) yields are given for illustration only;

(viii) reduced pressures are given as absolute pressures in pascals (Pa); other pressures are given as gauge pressure in bars;

(ix) chemical symbols have their usual meanings; the following abbreviations have also been used: v (volume), w (weight); mp (melting point), L [liters(s)], mL (milliliters), mM (millimoles), g [gram(s)], mg [milligram(s), min (minutes), h (hour);

(x) solvent ratios are given in volume: volume (v/v) terms; and (xi) end product names are correlated with formulae set out on pages following the Examples; values for $Y^1$-$Y^4$, $Z^1$-$Z^4$ and R are hydrogen unless otherwise stated.

EXAMPLE 1

Spiro[1,3-dihydroisoindole-1,1'-(1,2,3,4-tetrahydronaphthalene)] formula Ie, n=2)

To a cold (ice bath) stirred suspension of the lactam spiro[1,3-dihydroisoindole-1,1'-(1,2,3,4-tetrahydronaphthalene)]-3-one (0.61 g, 2.4 mM) in tetrahydrofuran (15 mL) under a nitrogen atmosphere was added lithium aluminum hydride (0.37 g, 9.8 mM). After stirring 5 min, the cooling bath was removed and the reaction mixture was refluxed for 18 hr and then cooled using an ice bath. To this cooled mixture was added dropwise in successive portions 0.37 mL of water, 0.37 mL of 15% aqueous hydroxide and 1.1 mL of water. The resulting mixture was filtered and the collected solids were washed several times with tetrahydrofuran. The filtrate and washes were combined, dried (sodium sulfate), filtered and concentrated to leave a yellow oil. This oil was chromatographed over silica gel (eluant: 1:2 ethyl acetate/hexane) to separate the title spiroisoindoline (0.43 g, 77%) as a pale yellow oil.

A portion (0.30 g, 1.3 mM) of the above chromatographed oil in 2 mL of ethanol was treated with ethereal hydrogen chloride. The resulting precipitate was collected and recrystallized from ethanol/diethyl ether (1:1) to given the hydrochloride salt of the spiroisondoline (0.24 g, 69%) as an off-white crystalline solid, mp 250°-251° C.

Analysis: C, 74.14; H, 6.73; N, 5.09 Calculated: C, 74.14; H, 6.73; N, 5.09 Found: C, 74.17; H, 6.72; N, 5.10

The starting spirolactam was obtained as follows:

a.
Spiro[1,3-dihydroisobenzofuran-1,1'-(1,2,3,4-tetrahydronaphthalene)]-3-one To a cold (ice bath) stirred solution of N-methylbenzamide (8.65 g, 64.0 mM) in dry tetrahydrofuran (190 mL) under a nitrogen atmosphere was added 2.58 M n-butyllithium (50.8 mL, 131 mM) in hexane over a 10 min period. After 1.5 hr, the resulting light red solution of dilithium salt intermediate (formula VI) was cooled using a dry ice/acetone bath and then treated over a 10 min period with a-tetralone (9.82 g, 67.2 mM) in dry etrahydrofuran (25 mL). After 45 min the cooling bath was removed and the reaction mixture was allowed to warm to 0° C. The reaction mixture was poured into 400 mL of ice water and the resulting mixture stirred for 15 min and then refluxed 45 min. After cooling, the mixture was filtered to separate 4.62 g of the desired spirolactone as an off-white solid. The filtrate was extracted with diethyl ether and the combined extracts were dried (magnesium sulfate), filtered and concentrated to leave an oil containing a suspended solid. This material was triturated with hexane/diethyl ether (2:1) and then filtered to separate an additional 3.90 g (total yield, 53%) of the spiroactone as a light tan solid. Recrystallization of a small portion of this solid from toluene/hexane (1:1) provided an analytical sample of the spirolactone as an off-white solid, mp 133°–133.5° C.

Analysis for C17H14O2; Calculated: C, 81.58; H, 5.64. Found: c, 81.40; H, 5.74.

b. Spiro[1,3-dihydroisoindole-1,1'-(1,2,3,4-tetrahydronaphthalene)]-3-one

A solution of the spirolactone produced in Example 1a (3.68 g, 14.7 mM) in 93 mL of ethanol was added to a solution of ammonium chloride (3.93 g, 73.5 mM) in 289 mL of 28% aqueous ammonium hydroxide. The resulting mixture was cooled in an ice bath, saturated with ammonia gas, placed in a stainless steel pressure vessel and heated to 232°–240° C. (1200 psi) for 20 hr. After cooling to room temperature, the contents of the pressure vessel were removed and concentrated. The residue was suspended in an ethyl acetate/water mixture, filtered and the filtrate extracted three times with ethyl acetate. The combined extracts were dried (sodium sulfate), filtered to remove some insoluble material and concentrated to give an amber oil. The oil was chromatographed over silica gel (eluant: diethyl ether) to give 1.77 g of a foam which was a mixture of 2-(5,6-dihydronaphthalen-8-yl)benzamide and the desired spirolactam, and 0.18 g of pure spirolactam which crystallized from diethyl ether as an off-white crystalline solid, mp 236.5°–240° C.

Analysis for C17H15NO.: Calculated: C, 81.9; H, 6.06; N, 5.62. Found: C, 81.86; H, 6.15; N, 5.22.

By treating the mixture isolated above with trifluoroacetic acid, the benzamide was converted to the spirolactam which was then isolated and purified. This conversion was carried out in the following manner: The 1.77 g of the mixture isolated above was refluxed in trifluoroacetic acid (40 mL) for 3 hr. cooled and concentrated to leave a dark oil. The oil was treated with saturated aqueous sodium bicarbonate and ether to provide a suspension which was filtered to separate a solid. The solid was washed with water and air dried to give a tan solid. Chromatography of this material over silica gel (eluant: diethyl ether) provided 1.45 g (total yield from the spirolactone, 44.5%) of the desired spirolactam as a yellow solid identical to that isolated above.

EXAMPLE 2

2-Methylspiro[1,3-dihydroisoindole-1,1'-(1,2,3,4-tetrahydronaphthalene)] (formula Ie; n=2; R=CH3)

A solution of the spiroisoindoline produced in Example 1 (0.328 g, 1.40 mM) in formic acid (0.71 mL) was treated with water (0.86 mL) and 37% aqueous formaldehyde (0.27 g, 3.4 mM). After heating and resulting solution at 84° C. for 0.5 hr., it was cooled to room temperature, added to excess aqueous saturated sodium bicarbonate which was then extracted with diethyl ether. The combined extracts were dried (sodium sulfate), filtered and concentrated to leave 0.35 g of a colorless oil. Flash chromatography of this oil over silica gel (eluant: 3:1 hexane: diethyl ether) gave a solution of the title spiroisoindoline which was treated with exess ethereal oxalic acid followed by enough ethanol to provide a free flowing crystalline solid. The solid was collected, washed with diethyl ether and air dried to give the oxalate salt of the title spiroisoindoline as a white solid. Recrystallization of this material from ethanol/diethyl ether provided the oxalate salt (0.35 g, 75%) as a white solid, mp 180°–182° (dec).

Analysis for C18H19N.(HO2C)2.0.2 H2 O: Calculated: C, 70.04; H, 6.29; N, 4.08. Found: C, 70.18; H, 6.29; N, 3.94.

EXAMPLE 3

2-Propylspiro[1,3-dihydroisoindole-1,1'-(1,2,3,4-tetrahydronaphthalene)] (formula Ie; N=2; R=CH2CH2CH3).

A stirred solution of the spiroisoindoline produced in Example 1 (0.33 g, 1.3 mM) in dimethylformamide (2.2 mL) was treated with potassium carbonate (0.51 g, 3.7 mM) and 1-iodopropane (0.22 g, 1.3 mM). After heating this mixture at 70° C. for 1 hr., an additional amount of 1-iodopropane (0.24 g, 1.4 mM) was added and the mixture stirred another hour at 70° C. The mixture was then filtered and the filtrate concentrated. The residue was dissolved in diethyl ether, washed with water, dried (sodium sulfate), filtered and concentrated to provide a yellow oil. Flash chromatography of this material over silica gel (eluant: 3:2 hexane:diethyl ether) gave the title spiroisoindoline as a colorless oil. The oil was dissolved in diethyl ether and the resulting solution treated with excess ethereal oxalic acid to form a gum. This material was triturated several times with diethyl ether and then treated with acetonitrile to provide a free flowing crystalline solid. The solid was collected and recrystallized from acetonitrile to give the oxalate salt of the title spiroisoindoline (0.30 g, 63%) as white crystals, mp 100°–106° C.

Analysis for C20H23N.(HO2C)2.CH3CN.0.2 H2O: Calculated: C, 69.95; H, 6.95; N, 6.80. Found: C, 70.05; H, 6.87; N, 6.56.

EXAMPLE 4

6-Methoxyspiro[1,3-dihydroisoindole-1,1'-(1,2,3,4-tetrahydronaphthalene)] (formula Ie; n=2; Y3=OCH3)

To a cold (ice bath) stirred solution of the spirolactam 6-methoxyspiro[1,3-dihydroisoindole-1,1'-(1,2,3,4-tetrahydronaphthalene) ]-3-one (4.30 g, 15.4 mM) in tetrahydrofuran (90 mL) under a nitrogen atmosphere was added in portions lithium aluminum hydride (2.34 g, 61.6 mM). After refluxing the resulting mixture for 18 hr., it was cooled and an additional quantity of lithium aluminum hydride (2.34 g, 61.6 mM) added. The mixture was refluxed an additional 20 hr., cooled (ice bath), and cautiously treated successively with water (4.7 mL), 10% aqueous sodium hydroxide (4.7 mL) and water (10 mL). The resulting mixture was treated with sodium sulfate until the suspended solids became granular. The mixture was filtered and the collected solids washed five times with tetrahydrofuran. The combined filtrate and washes were concentrated to an oil which was dissolved in diethyl ether and treated with a solution of 36% hydrochloric acid (1.36 mL, 1.58 mM) in 100 mL water. The ether layer was separated and the aqueous layer washed three times with diethyl ether. After basification of the aqueous layer with sodium bicarbonate, it was extracted with ethyl acetate and the combined extracts were dried (sodium sulfate), filtered and concentrated to provide the title spiroisoindoline (3.63 g, 88%) as a colorless oil. A portion of this oil (0.59 g, 2.2 mM) was dissolved in diethyl ether and treated with ethereal hydrogen chloride whereupon a white precipitate formed. The solid was collected and then recrystallized from ethanol/diethyl ether to give the hydrochloride salt of the title spiroisoindoline (0.47 g, 68%) as a white crystalline solid, mp 233°–233.5° C.

Analysis of $C_{18}H_{19}NO.HCl.0.15\ C_2H_5OH.0.15\ H_2O$: Calculated: C, 70.58; H, 6.86; N, 4.50. Found: C, 70.61; H, 6.85; N, 4.45.

The starting spirolactam was obtained as follows:

6-Methoxyspiro[1,3-dihydroisobenzofuran-1,1'-(1,2,3,4-tetrahydronaphthalene)]-3-one To a cold (ice bath) stirred solution of 4-methoxy-N-methylbenzamide (8.60 g, 5.21 nM) in dry tetrahydrofuran (155 mL) under a nitrogen atmosphere was added 2.05M n-butyllithium (41.4 mL, 107 mM) in hexane over a 10 min period. After 1.5 hr., the resulting solution of the dilithium salt intermediate (formula VI; $Y^3=OCH_3$) was cooled using a dry ice/acetone bath and then treated over a 5 min period with a solution of 1-tetralone (8.00 g, 54.7 mM) in tetrahydrofuran (20 mL). After 20 min the cooling bath was removed and the reaction mixture was allowed to warm to 0° C. over a 30 min period. After an additional 30 min at 0° C., the reaction mixture was poured into ice cold water (400 mL) and the resulting mixture refluxed for 20 min. The reaction mixture was then cooled by adding ice and the pH adjusted to 6 by the addition of aqueous hydrochloric acid (10%). After extracting the resulting mixture with diethyl ether, the combined extracts were dried (sodium sulfate), filtered and concentrated to give an amber oil. This oil was chromatographed over silica gel (eluant: 1:2 diethyl ether/hexane) to separate the title spirolactone (6.35 g, 43%) as a pale violet from which slowly crystallized. A small portion (0.11 g) of this material was recrystallized from toluene/hexane to give an analytical sample of the spirolactone (0.10 g) as white crystals, mp 106.5°–107° C.

Analysis for $C_{18}H_{16}O_3$: Calculated: C, 77.13; H, 5.75. Found: C, 77.03; H, 5.84.

b.
6-Methoxyspiro[1,3-dihydroisoindole-1,1'-(1,2,3,4-tetrahydronaphthalene)]-3-one To a stirred cold (ice bath) suspension of anhydrous (dried at 120° C. for 20 min) ammonium chloride (4.58 g, 85.6 mM) in anhydrous toluene (133 mL) under a nitrogen atmosphere was added over 15 min 2.0M trimethylaluminum (42.8 mL, 85.6 mM) in hexane. The mixture was then stirred at room temperature until no further evolution of gas was observed. The resulting organoaluminum reagent was added over 5 min to a stirred solution of the spirolactone provided in Example 4a (6.00 g, 21.4 mM) in toluene (60 mL). After heating the resulting mixture at 54° C. for 42 hr., it was cooled to ambient temperature and transferred by cannula to cold 3% aqueous hydrochloric acid (150 mL). The mixture was treated with ice and saturated aqueous sodium bicarbonate until the approximate pH was 6.5. After adding a few drops of 10% aqueous hydrochloric acid to dissolve some residual aluminum salts, the reaction mixture was extracted with ethyl acetate (3 times) and diethyl ether (1 time). The combined extracts were dried (sodium sulfate), filtered and concentrated to give an approximate 3:1 mixture of 6-methoxyspiro[1,3-dihydroisobenzofuran-1,1'-(1,2,3,4-tetrahydronaphthalene)]-3-imine and 2-(5,6-dihydronaphthanlen-8-yl)-4-methoxybenzamide, respectively, as a light tan foam (6.32 g).

The above mixture was refluxed under a nitrogen atmosphere in trifluoroacetic acid (100 mL) for 5 hr. The reaction mixture was cooled and concentrated to leave an oil which was treated with saturated aqueous sodium bicarbonate to give a suspension. The mixture was filtered and the collected solid was washed with water and air dried to give a tan solid which was chromatographed over silica gel (eluant: 2:1 diethyl ether/hexane followed by ethyl acetate). The fractions containing the desired material were concentrated to provide the title spirolactam (4.36 g, 73%) as a light tan solid. An analytical sample was obtained by crystallization of a small portion from diethyl ether/hexane to give the spirolactam as white crystals, mp 22.5°–223.5° C.

Analysis for $C_{18}H_{17}NO_2$: Calculated: C, 77.40; H, 6.13; N, 5.01. Found: C, 77.26; H, 6.15; N, 4.94.

EXAMPLE 5

Spiro[1,3-dihydroisoindole-1,1'-(1,2,3,4-tetrahydronaphthalene)]-6-ol (formula Ie; n=2; $Y^3=OH$)

A solution of the spiroisoindoline produced in Example 4 (0.62 g, 2.3 mM) in methylene chloride (11 mL) was added over a 5 min period to a cold (ice bath) stirred solution of boron tribromide (1.76 g, 7.0 mM) in methylene chloride (8 mL). After stirring the resulting mixture for 30 min at 0° C., it was added dropwise with stirring to excess cold saturated aqueous sodium bicarbonate. The mixture was then extracted with chloroform and the combined extracts were dried (sodium sulfate), filtered and concentrated to leave a white foam. Chromatography of this material over silica gel eluant: 2:1 diethylether/hexane) provided the title compound as a white foam (0.61 g, 82%). A portion of this material was crystallized from diethyl ether/ethyl acetate to give an analytical sample of the compound as a white solid, mp 158°–159° C.

Analysis for $C_{17}H_{17}NO.0.10\ (C_2H_5)_2O$: Calculated: C, 80.77; H, 7.01; N, 5.41. Found: C, 80.40; H, 7.01; N, 5.29.

The hydrochloride salt of the title compound was prepared by treating an ethereal solution of the compound (0.40 g, 1.6 mM) with thereal hydrogen chloride. The resulting solid which precipitated was collected and recrystallized from ethanol/diethyl ether to provide the hydrochloride salt as off-white crystals (0.32 g, 69%), mp 298°–299° C.

Analysis for $C_{17}H_{17}NO.HCl$: Calculated: C, 70.95; H, 6.30; N, 4.87. Found: C, 70.57; H, 6.37; N, 4.86.

EXAMPLE 6

6-methoxy-2-methylspiro[1,3-dihydroisoindole-1,1'-(1,2,3,4-tetrahydronaphthalene)] (formula Ie, n=2; R=$CH_3$; $Y^3=OCH_3$).

A solution of the spiroisoindoline produced in Example 4 (0.43 g, 1.6 mM) in formic acid (0.80 mL) was treated with water (1 mL) and 37% aqueous formaldehyde (0.32 g, 3.9 mM) and then heated under nitrogen at 80° C. for 30 min. After cooling to room temperature, the reaction mixture was added to excess saturated aqueous sodium bicarbonate and the resulting mixture extracted with ethyl acetate. The combined extracts were dried (sodium sulfate), filtered and concentrated to leave an oil. The oil was chromatographed (eluant: 1:1 diethyl ether/hexane) and the fractions containing the desired product were combined and treated with excess ethereal oxalic acid. The resulting gum which precipitated was treated with acetonitrile/diethyl ether to provide a solid. Recrystallization from ethanol/diethyl ether provided the oxalate salt of the title compound as white crystals (0.46 g, 77%), mp 171°–173.5° C.

Analysis of $C_{19}H_{21}NO \cdot (CO_2H)_2 \cdot 0.2\ H_2O$: Calculated: C, 67.62; H, 6.32; N, 3.75. Found: C, 67.87; N, 6.36; N, 3.65.

EXAMPLE 7

2-Methylspiro[1,3-dihydroisoindole-1,1'-(1,2,3,4-tetrahydronaphthalene)]-6-ol (formula Ie; n=2; R=CH$_3$; Y$^3$=OH)

A solution of the compound produced in Example 5 (0.53 g, 2.1 mM) in formic acid (1.05 mL) was treated with water (1.3 mL) and 37% aqueous formaldehyde (0.41 g, 5.1 mM). The stirred solution was heated at 80° C. for 35 min and then cooled to room temperature and poured into excess saturated aqueous sodium bicarbonate. The resulting mixture was extracted with ethyl acetate and the combined extracts were dried (sodium sulfate), filtered and concentrated to leave a colorless oil. This material was chromatographed over silica gel (eluant: 1:1 diethyl ether/hexane) and the fractions containing the desired product were combined and treated with excess ethereal oxalic acid. The resulting precipitated gum was triturated three times with diethyl ether and the resulting solid was collected and air dried to give a white solid. Recrystallization of this material from ethanol gave the oxalate salt of the title compound as a white solid (0.38 g, 68%), mp 243.5°–245° C.

Analysis for $C_{18}H_{19}NO \cdot 0.5\ (CO_2H)_2$: Calculated: C, 73.53; H, 6.49; N, 4.51. Found: C, 73.27; H, 6.50; N, 4.42.

EXAMPLE 8

Spiro[6,7,8,9-tetrahydro-5H-benzocycloheptene-5,1'-(1,3-dihydroisoindole)] (formula Ie; n=13).

To a stirred solution of the lactam spiro-[6,7,8,9-tetrahydro-5H-benzocycloheptene-5,1'-(1,3-dihydroisoindole)]-3'-one (0.82 g, 3.11 mM) in tetrahydrofuran (75 mL) was added lithium aluminum hydride (0.62 g, 16.3 mM). The resulting mixture was refluxed for two days under a nitrogen atmosphere, cooled, and quenched by carefully adding 0.62 mL water, 0.62 mL 15% aqueous sodium hydroxide and 1.86 mL water in successive portions. The resulting mixture was filtered and the collected solids washed thoroughly with methylene chloride. The combined filtrate and washes were concentrated and flash chromatographed over silica gel (eluant: 2:1 hexane:diethyl ether) to provide the title compound as a white solid (0.55 g, 71%). Treatment of this material (0.51 g, 2.05 mM) with ethereal hydrogen chloride gave white solids which were recrystallized from ethanol/diethyl ether to provide the hydrochloride salt of the title compound as white crystals (0.54 g, 91%), mp 294.5°–295° C.

Analysis for $C_{18}H_{19}N \cdot HCl \cdot 0.2H_2O$: Calculated: C, 74.70; H, 7.10; N, 4.84. Found: C, 74.68; H, 7.11; n, 4.65.

The starting lactam was prepared as follows:

a. Spiro[6,7,8,9-tetrahydro-5H-benzocycloheptene-5,1'-(1,3-dihydroisobenzofuran)]-3'-one Using a procedure similar to that described in Example 1a except adding 1-benzosuberone to the solution of dilithiated benzamide, the title compound was obtained as a white crystalline solid (46%), mp 150°–151° C. Analysis for $C_{18}H_{16}O_2$: Calculated: C, 81.79; H, 6.10. Found: C, 81.97; H, 6.08.

b. Spiro[6,7,8,9-tetrahydro-5H-benzocycloheptene-5,1'-(1,3-dihydroisoindole)]03'-one Using a procedure similar to that described in Example 4b except starting with the spirolactone produced in Example 8a, a mixture of spiro[6,7,8,9-tetrahydro-5H-benzocycloheptene-5,1'-(1,3-dihydroisobenzofuran)-3+-imine and 2-(6,7-dihydro-5H-benzocyclohepten-9-yl)benzamide (approximately 4:1) was obtained as a white solid (97%). When this mixture was treated with trifluoroacetic acid in a manner similar to that described in Example 4b, a white solid was obtained and recrystallized from ethanol to provide the desired spirolactone as white crystals (96%), mp 233°–234° C.

Analysis for $C_{18}H_{17}NO$: Calculated: C, 82.10; H, 6.51; N, 5.32. Found: C, 81.92; H, 6.57; N, 5.23.

EXAMPLE 9

2'-Methylspiro[6,7,8,9-tetrahydro-5H-benzocycloheptene-5,1'-(1,3-dihydroisoindole)] (formula Ie; n=3; R=CH$_3$).

Using a procedure similar to that described in Example 2 except starting with the compound produced in Example 8, the oxalate salt of the title compound was obtained as white crystals (91%), mp 176°–176.5° C.

Analysis for $C_{19}H_{21}N \cdot (CO_2H)_2$: Calculated: C, 71.37; H, 6.56; N, 3.96. Found: C, 71.15; H, 6.59; N, 4.18.

EXAMPLE 10

2'-Propylspiro[6,7,8,9-tetrahydro-5H-benzocycloheptene-5,1'-(1,3-dihydroisoindole)] (formula Ie; n=3; R=CH$_2$CH$_2$CH$_3$)

Using a procedure similar to that described in Example 3 except starting with the compound produced in Example 8 and recrystallizing from acetonitrile/diethyl ether, the oxalate salt of the title compound was obtained as white crystals (41%), mp 116°–119° C.

Analysis for $C_{21}H_{25}N \cdot (CO_2H)_2 \cdot 0.9CH_3CN \cdot 0.2\ H_2O$: Calculated: C, 70.58; H, 7.19; N, 6.31. Found: C, 70.52; H, 7.08; N, 6.32.

EXAMPLE 11

6'-Methoxyspiro[6,7,8,9-tetrahydro-5H-benzocycloheptene-5,1'-(1,3-dihydroisindole)] (formula Ie; n=3; Y$^3$=OCH$_3$)

Using a procedure similar to that described in Example 8, except starting with the spirolactam produced in Example 11b, the hydrochloride salt of the title compound was obtained as a white crystalline solid (83%), mp 280.5°–281.5° C.

Analysis for $C_{19}H_{21}NO \cdot HCl \cdot 0.3H_2O$: Calculated: C, 71.04; H, 7.09; N, 4.36. Found: C, 71.08; H, 6.97; N, 4.32.

The starting lactam 6'-methoxyspiro[6,7,8,9-tetrahydro-5H-benzocycloheptene-5,1'-(1,3-dihydroisoindole)]-3'-one was obtained as follows:

a. 6'-Methoxyspiro[6,7,8,9-tetrahydro-5H-benzocycloheptene-5,1'-(1,3-dihydroisobenzofuran)]-3'-one Using a procedure similar to that described in Example 4a except adding 1-benzosuberone to the solution of dilithiated salt intermediate and recrystallization from toluene, the title compound was obtained as a white crystalline solid (22%), mp 145°–146.5° C.

Analysis for $C_{19}H_{18}O_3$: Calculated: C, 77.53; H, 6.16. Found: C, 77.33; H, 6.16.

b. 6'-Methoxyspiro[6,7,8,9-tetrahydro-5H-benzocycloheptene-5,1'-(1,3-dihydroisoindole)]-3'-one Using a procedure similar to that described in Example 4b except starting with the spirolactone produced in Example 11a, a mixture of 2-(6,7-dihydro-5H-benzocyclohepten-9-yl)-4-methoxybenzamide and 6'-methoxyspiro[6,7,8,9-tetrahydro-5H-benzocycloheptene-5,1'-(1,3-dihydroisobenzofuran)-3'-imine (approximately 1:4) was obtained as a yellow solid (100%). When this mixture was treated with trifluoroacetic acid in a manner similar to that described in Example 4b, a white solid was obtained and was recrystallized from ethyl acetate to provide the desired spirolactam as white crystals (60%). mp 189°–189.5° C.

Analysis for $C_{19}H_{19}NO_2$: Calculated: C, 77.79; H, 6.53; N, 4.77. Found: C, 77.67; H, 6.54; N, 4.68.

EXAMPLE 12

6'-Methoxy-2'-methylspiro[6,7,8,9-tetrahydro-5H-benzocycloheptene-5,1'-(1,3-dihydroisoindole)] (formula Ie; n=3; R=CH$_3$; Y$^3$=OCH$_3$)

Using a procedure similar to that described in Example 6 except starting with the compound produced in Example 11, the oxalate salt of the title compound was obtained as white crystals (66%), mp 179.5°–180° C.

Analysis for $C_{20}H_{23}NO\cdot(CO_2H)_2$: Calculated: C, 68.91; H, 6.57; N, 3.65. Found: C, 68.70; H, 6.50; N, 3.52.

EXAMPLE 13

2'-Methylspiro[6,7,8,9-tetrahydro-5H-benzocycloheptene-5,1'-(1,3-dihydroisoindole)]-6'-ol (formula Ie; n=3; R=CH$_3$; Y$^3$=OH)

A solution of the compound produced in Example 12 (0.36 g, 1.23 mM) in methylene chloride (8 mL) was added dropwise to a stirred solution of boron tribromide (0.64 g, 2.58 mM) in methylene chloride (3 mL). After stirring for 0.5 hr, the reaction mixture was quenched with aqueous sodium bicarbonate and then extracted with methylene chloride. The methylene chloride extracts were filtered to separate some undissolved solids and then concentrated to leave a residue which was chromatographed over silica gel (eluant: 3:1 hexane/diethyl ether followed by diethyl ether) to provide the title compound (0.125 g, 39%) as a white solid. The hydrochloride salt of the title compound was prepared by treating a diethyl ether solution of this solid (0.09 g, 0.32 mM) with ethereal hydrogen chloride, collecting the resulting solid and recrystallizing from ethanol/diethyl ether to give white crystals (0.09 g, 91%), mp 247.5°–249° C.

Analysis for $C_{19}H_{21}NO\cdot HCl\cdot 0.59\ H_2O$: Calculated: C, 69.90; H, 7.15; N, 42.9. Found: C, 69.90; H, 7.10; N, 4.17.

EXAMPLE 14

6'-Methoxy-2'-propylspiro[6,7,8,9-tetrahydro-5H-benzocycloheptene-5,1'-(1,3-dihydroisoindole)] (formula Ie; n=3; R=CH$_2$CH$_2$CH$_3$; Y$^3$=OCH$_3$)

Using a procedure similar to that described in Example 3 except starting with the compound produced in Example 11 and a large excess of iodopropane, the oxalate salt of the title compound was obtained and recrystallized from acetonitrile/diethyl ether to provide white crystals (68%), mp 148.5°–149° C.

Analysis for $C_{22}H_{27}NO\cdot(CO_2H)_2\cdot 0.3H_2O$: Calculated: C, 69.14; H, 7.16; N, 3.36. Found: C, 69.17; H, 7.02; N, 3.38.

EXAMPLE 15

Spiro[indan-1,1,'-(1,3-dihydroisoindole)] (formula Ie; n=1)

To a stirred refluxing solution of the lactam spiro[indan-1,1'-(1,3-dihydroisoindole)]-3'-one (0.30 g, 1.32 mM) in dry tetrahydrofuran (5 mL) was slowly added borane dimethylsulfide (0.28 g, 3.7 mM). The reaction flask was fitted with a small distillation apparatus and dimethylsulfide was removed by distillation while adding dry tetrahydrofuran to the reaction flask to maintain the volume between 2–5 mL. Two additional portions of borane dimethylsulfide (each portion=0.28 g, 3.7 mM) were added to the reaction mixture during a 6 hr period with constant removal of dimethyl sulfide during this time period. The reaction mixture was then refluxed 24 hr, cooled and quenched by adding 1.4 mL of 6N HCl. After heating for 0.5 hr, the reaction mixture was extracted with methylene chloride and the combined extracts dried (MgSO$_4$), filtered and concentrated to leave a yellow solid (0.28 g) consisting of a 1:1 mixture of the starting lactam and the title compound.

To a stirred solution of the above mixture (0.28 g, ca. 1.2 mM) in tetrahydrofuran (20 mL) under a nitrogen atmosphere was added lithium aluminum hydride (0.15 g, 3.9 mM). After refluxing the resulting mixture for 18 hr, it was cooled and quenched by the sequential addition of water (0.15 mL), 15% aqueous sodium hydroxide (0.15 mL) and water (0.45 mL). The resulting mixture was stirred for 1 hr and filtered. The collected solids were washed with methylene chloride and the filtrate and washes were combined and concentrated. The residue was chromatographed over silica gel (eluant: 1:3 hexane/diethyl ether) to provide the title compound as a white solid (0.25 g, 92%). By adding ethereal hydrogen chloride to a solution of the title compound in diethyl ether, the hydrochloride salt of the title compound was obtained (82%) as white crystals, mp 210.5°–213° C.

Analysis for $C_{16}H_{15}N\cdot HCl\cdot 0.2H_2O$: Calculated: C, 73.53; H, 6.32; N, 5.36. Found: C, 73.49; H, 6.20; N, 5.31.

The starting lactam was obtained as follows:

a. Spiro[indan-1,1'-(1,3-dihydroisobenzofuran)]3'-one.

Using a procedure similar to that described in Example 1a except adding 1-indanone to the solution of dilithiated benzamide, the desired spirolactone wa obtained as a light gray solid (34%), mp 138°–139° C.; MS(CI): 237 (M+H).

b. Spiro[indan-1,1'-(1,3-dihydroisoindole)]-3'-one

A mixture of the spirolactone produced in Example 15a (0.48 g, 2.0 mM), ammonium chloride (0.54 g, 10 mM) and 28% aqueous ammonium hydroxide (45 mL) was heated at 280° C. (1420 psi) for 22 hr in a stainless steel pressure vessel. The reaction mixture was then concentrated and the residue chromatographed over silica gel (eluant: 1:3 hexane/diethyl ether) to obtain the desired spirolactam (0.29 g, 61%) as a white solid, mp 205°–206.5° C.; MS(CI): 236 (M+H).

EXAMPLE 16

2'-Methylspiro[indan-1,1'-(1,3-dihydroisoindole)]. (formula Ie; n=1; R=CH$_3$)

Using a procedure similar to that described in Example 2 except starting with the compound procedure in Example 15, the oxalate salt of the title compound was obtained as white crystals (81%), mp 163.5°–164.5° C.

Analysis for C$_{17}$H$_{17}$N·(CO$_2$H)$_2$·0.15H$_2$O: Calculated: C, 69.56; H, 5.93; N, 4.27. Found: C, 69.56; H, 5.92; N, 4.18.

EXAMPLE 17

2'-Propylspiro[indan-1,1'-(1,3-dihydroisoindole)](formula Ie; n=1; R=CH$_2$CH$_2$CH$_3$)

Using a procedure similar to that described in Example 3 except starting with the compound produced in Example 15 and recrystallizing from acetonitrile/diethyl ether, the oxalate salt of the title compound was obtained as white crystals (82%), mp 91°–95° C.

Analysis for C$_{19}$H$_{21}$N·(CO$_2$H)$_2$·0.5CH$_3$CN·0.5H$_2$O: Calculated: C, 69.00; H, 6.71; N, 5.49. Found: C, 68.92; H, 6.49; N, 5.56.

EXAMPLE 18

4-Methoxyspiro[indan-1,1'-(1,3-dihydroisoindole)](formula Ie; n=1; Z$^4$=OCH$_3$)

Using a procedure similar to that described in Example 1 except using the spirolactam 4-methoxyspiro[indan-1,1'-(1,3-dihydroisoindole)]-3'-one as the starting material, the hydrochloride salt of the title compound was obtained (76%) as a light tan solid, mp 237°–238.5° C.

Analysis for C$_{17}$H$_{17}$NO·HCl·0.15H$_2$O: Calculated: C, 70.29; H, 6.35; N, 4.82. Found: C, 70.29; H, 6.32; N, 4.62.

The starting spirolactam was obtained as follows:

a.
4-Methoxyspiro[indan-1,1'-(1,3-dihydroisobenzofuran)]-3'-one.

Using a procedure similar to that described in Example 1a except adding 4-methoxy-1-indanone to the solution of the dilithiated benzamide, the desired spirolactone was obtained (15%) as a white crystalline solid, mp 111°–112.4° C.

Analysis for C$_{17}$H$_{14}$O$_3$: Calculated: C, 76.68; H, 5.30. Found: C, 76.44; H, 5.29.

b. Spiro[indan-1,1'-(1,3-dihydroisoindole)]-4-ol-3'-one

A mixture of the spirolactone produced in Example 18a (1.2 g, 4.5 mM) and 28% aqueous ammonium hydroxide (100 mL) was heated with stirring in a stainless steel pressure vessel at 280° C. for 22 hr. The reaction vessel was allowed to cool to room temperature and the reaction mixture removed and concentrated. A second reaction was carried out using the spirolactone of Example 18a (0.5 g, 1.9 mM), ammonium chloride (0.54 g, 9.4 mM) and 28% aqueous ammonium hydroxide (50 mL). After heating this mixture in a stainless steel pressure vessel at 280° C. for 22 hr, it was cooled to room temperature and concentrated. The residues from both reactions were combined, triturated with methylene chloride and filtered to separate a brown solid. Chromatography of this solid over silica gel (eluant: 2:1 hexane/diethyl ether) provided the spirolactam (0.77 g, 55%), mp 324°–325° C.

Analysis for C$_{16}$H$_{13}$NO$_2$·O—3H$_2$O: Calculated: C, 74.87; H, 5.34; N, 5.45. Found: C, 74.96; H, 5.37; N, 5.31.

c.
4-Methoxyspiro[indan-1,1'-(1,3-dihydroisoindole)]-3'-one

A stirred mixture of the spirolactam produced in Example 18b (0.45 g, 1.8 mM) and potassium carbonate (0.99 g, 7.2 mM) in dimethylformamide (45 mL) was heated to 50° C. and then allowed to cool to room temperature. Iodomethane (1.53 g, 10.8 mM) was added and the resulting mixture stirred at room temperature for 18 hr. The mixture was filtered and the collected solids washed with methylene chloride. The combined filtrate and washes were concentrated and the residual brown solid chromatographed over silica gel (eluant: 1:1 hexane/diethyl ether) to provide the desired spirolactam (0.45 g, 96%) as a light tan solid, mp 222.5°–224° C.

Analysis for C$_{17}$H$_{15}$NO$_2$·0.75H$_2$O: Calculated: C, 73.23; H, 5.96; N, 5.02. Found: C, 73.27; H, 5.60; N, 4.99.

EXAMPLE 19

Spiro[indan-1,1'-(1,3-dihydroisoindole)]-4-ol (formula Ie; n=1; Z$^4$=OH).

Using a procedure similar to that described in Example 13 except starting with the compound produced in Example 18, the hydrochloride salt of the title compound was obtained (61%) as white crystals, mp 310°–311° C.

Analysis for C$_{16}$H$_{15}$NO·HCl·0.15H$_2$O: Calculated: C, 69.50; H, 5.94; N, 5.06. Found: C, 69.51; H, 6.05; N, 4.92.

EXAMPLE 20

Spiro[4,5,6,7-tetrahydrobenzothiophene-4,1'-(1,3-dihydroisoindole)](formula If; n=2; X=S)

Using a procedure similar to that described in Example 1 except starting with the spirolactam spiro[4,5,6,7-tetrahydrobenzothiophene-4,1'-(1,3-dihydroisoindole)]-3'-one, the hydrochloride salt of the title compound was obtained (51%) as white crystals, mp 268.5°–269.5° C.

Analysis for C$_{15}$H$_{15}$NS·HCl·0.1H$_2$O: Calculated: C, 64.43; H, 5.84; N, 5.01. Found: C, 64.43; H, 5.96; N, 4.87.

The starting lactam was obtained as follows:

a.
Spiro[4,5,6,7-tetahydrobenzothiophene-4,1'-(1,3-dihydroisobenzofuran)]-3'-one Using a procedure similar to that described in Example 1a except adding 4-keto-4,5,6,7-tetrahydrothianaphthalene to the solution of the dilithiated benzamide, the desired spirolactone was obtained (57% yield) as a white crystalline solid, mp 173.5°–174.5° C.

Analysis for C$_{15}$H$_{12}$O$_2$S: Calculated: C, 70.29; H, 4.72. Found: C, 70.16; H, 4.75.

b.
Spiro[4,5,6,7-tetrahydrobenzothiophene-4,1'-(1,3-dihydroisoindole)]-3'-one Using a procedure similar to that described in Example 4b except starting with the compound produced in Example 20a, a mixture of 2-(6,7-dihydrobenzothiophen-4-yl)benzamide and spiro[4,5,6,7-tetrahydro-benzothiophene-4,1'-(1,3-dihydroisobenzofuran)]-3'-imine (approximately 1:1) was obtained as a white solid. When this mixture was treated with trifuloroacetic acid in a manner similar to that described in Example 4a, the desired spirolactam was obtained (79%) as a light orange-brown solid. Recrystallization of a portion of this solid from ethanol/diethyl ether provided an analytical sample of the spirolactam as light yellow crystals, mp 224°–226° C.

Analysis for $C_{15}H_{13}NOS \cdot 0.57H_2O$: Calculated: C, 67.83; H, 5.36; N, 5.27. Found: C, 67.89; H, 5.00; N, 5.12.

EXAMPLE 21

2'-Methylspiro[4,5,6,7-tetrahydrobenzothiophene-4,1'-(1,3-dihydroisoindole)](formula If; n=2; R=$CH_3$; X=S)

Using a procedure similar to that described in Example 2 except starting with the compound produced in Example 20, the oxalate salt of the title compound was obtained as white crystals (69%), mp 173.5°–174.5° C.

Analysis for $C_{16}H_{17}NS \cdot (CO_2H)_2 \cdot 0.15H_2O$: Calculated: C, 62.10; H, 5.59; N, 4.02. Found: C, 62.08; H, 5.53; N, 3.98.

EXAMPLE 22

2'-Propylspiro[4,5,6,7-tetrahydrobenzothiophene-4,1'-(1,3-dihydroisoindole)](formula If; n=2; R=$CH_2CH_2CH_3$; X=S)

Using a procedure similar to that described in Example 3 except starting with the compound produced in Example 20, the oxalate salt of the title compound was obtained (78%) as white crystals, mp 123.5°–125.5° C.

Analysis for $C_{18}H_{21}NS \cdot (CO_2H)_2 \cdot 0.95CH_3CN$: Calculated: C, 63.77; H, 6.32; N, 6.62. Found: C, 63.63; H, 6.30; N, 6.63.

EXAMPLE 23

This example illustrates the optical resolution of 2'-methylspiro-[4,5,6,7-tetrahydrobenzothiophene-4,1'-(1,3-dihydroisoindole)] (−)-2'-Methylspiro[4,5,6,7-tetrahydrobenzothiophene-4,1'-(1,3-dihydroisoindole)]

To a solution of racemic 2'-methylspiro[4,5,6,7-tetrahydrobenzothiophene-4,1'-(1,3-dihydroisoindole)] (1.63 g, 6.39 mM) in 5% aqueous ethanol (15 mL) was added a solution of (+)-2,3-di-p-toluoyl-D-tartaric acid (2.47 g, 6.39 mM) in 5% aqueous ethanol (15 mL). After adding an additional 1 mL of water to the resulting solution, it was allowed to stand for 0.5 hr. and then filtered to separate the resulting crystalline precipitate of enriched diastereomeric salt (1.99 g). On standing, an additional quantity (0.22 g) of crystalline material precipitated from the above filtrate and was isolated by filtration. On further standing, the filtrate from the second filtration provided additional tacky solids which were filtered off and recrystallized from 10% aqueous ethanol (20 mL) to provide a further quantity of crystalline material (0.60 g). The latter two crystalline fractions (total amount=0.82 g) were combined and recrystallized from 10% aqueous ethanol (15 mL) to give another portion of the enriched, but not pure, diastereomeric salt (0.38 g). This material (0.38 g) was combined with the initial crop of separated solids (1.99 g) and the resulting mixture recrystallized first from 10% aqueous ethanol (40 mL) and then twice from absolute ethanol (35 mL, 30 mL) to provide the pure diastereomeric salt (1.40 g).

The above pure diastereomeric salt (1.40 g, 2.18 mM) was added to saturated aqueous sodium bicarbonate (30 mL) and the resulting mixture extracted four times with diethyl ether. The combined extract were dried ($MgSO_4$) and filtered. The filtrate was treated with a solution of oxalic acid (0.20 g, 2.18 mM) in ethanol (10 mL) to form a precipitate. The precipitate was collected and recrystallized from absolute ethanol (35 mL) to give (−)-2'-methylspiro[4,5,6,7-tetrahydrobenzothiophene-4,1'-(1,3-dihydroisoindole)] oxalate (0.67 g) as a white crystalline solid, mp 204.5°–205.5° C.

$[\alpha]_D^{24} = -82°$ (c=0.0050, $CH_2Cl_2$).

Analysis for $C_{16}H_{17}NS \cdot HO_2CCO_2H$: Calculated: C, 62.59; H, 5.54; N, 4.06. Found: C, 62.77; H, 5.55; N, 4.05.

(+)-2'Methylspiro[4,5,6,7-tetrahydrobenzothiophene-4,1'-(1,3-dihydroisoindole)]

The filtrates from all (except the final two) of the above recrystallizations of the diastereomeric salt were combined and concentrated. The residue (2.60 g) was treated with saturated aqueous sodium bicarbonate (35 mL) and the resulting mixture extracted with four portions of diethyl ether. The combined extracts were concentrated to leave 2'-methylspiro[4,5,6,7-tetrahydrobenzothiophene-4,1'-(1,3-dihydroisoindole)] (1.01 g, 3.96 mM) enriched in the dextro (+)-enantiomer. This material was dissolved in 10% aqueous ethanol (20 mL) and treated with a solution of (−)-2,3-di-p-toluoyl-L-tartaric acid (1.80 g, 4.66 mM) in 10% aqueous ethanol (20 mL). After standing, a crystalline precipitate formed and was collected by filtration to give the enriched diastereomeric salt as a white solid (1.86 g). Recrystallization of this material from absolute ethanol (35 mL) gave a white crystalline solid (1.42 g). Additional quantities of crystalline solids obtained from the above filtrates were combined and recrystallized from absolute ethanol (15 mL) to provide another crop (0.32 g) of the enriched diastereomeric salt. The two crystalline fractions were combined (total quantity=1.74 g) and recrystallized twice from absolute ethanol (30 mL portions) to give the pure diastereomeric salt (1.45 g).

The above pure diastereomeric salt (1.45 g, 2.26 mM) was treated with saturated aqueous sodium bicarbonate (35 mL) and the resulting mixture extracted with four portions of diethyl ether. The combined extracts were dried ($MgSO_4$) and filtered. The filtrate was treated with a solution of oxalic acid (0.20 g, 2.26 mM) in ethanol (10 mL) to form a precipitate. The precipitate was collected and recrystallized from absolute ethanol (35 mL) to give (+)-2'-methylspiro[4,5,6,7-tetrahydrobenzothiophene-4,1'-(1,3-dihydroisoindole)] oxalate (0.72 g) as a white crystalline solid, mp 203.5°–204.5° C.

$[\alpha_D^{24}] = +86°$ (c=0.0050, $CH_2Cl_2$).

Analysis for $C_{16}H_{17}NS \cdot HO_2CCP_2H$: Calculated: C, 62.59; H, b 5.54; N, 4.06. Found: C, 62.32; H, 5.60; N, 3.98.

EXAMPLE 24

The following illustrate representative pharmaceutical dosage forms containing a compound of formula I, for example as illustrated in any of the previous Examples, (hereafter referred to as "compound X"), for thereapeutic or prophylactic use in humans:

(a) Injectable

Compound X is readily soluble in aqueous solutions prepared in a pH range of 3-5.

| Ingredient | Units/mL |
| --- | --- |
| Compound X | 10 mg |
| 1N HCl* | q.s.** |
| Water for Injection (WFI) q.s. ad*** | 1.0 mL |

*Added to adjust pH to 3-5
**q.s. = sufficient quantity
***q.s. ad = sufficient quantity of WFI is added to bring the final volume to 1.0 mL (b) Injectable Compound X is not readily soluble in aqueous solution.

| | Ingredient | Units/mL |
| --- | --- | --- |
| | Compound X | 10 mg |
| | Ethanol | 0.1 mL |
| | PEG 400* | 0.4 mL |
| | Water for Injection (WFI) q.s. ad** | 1.0 mL |
| (c) | Tablet | mg/tablet |
| | Compound X | 50.0 |
| | Lactose, NF | 223.75 |
| | Croscarmellose sodium | 6.0 |
| | Maize starch | 15.0 |
| | Polyvinylprrolidone (5% w/v paste) | 2.25 |
| | Magnesium stearate | 3.0 |
| (d) | Capsule | |
| | Compound X | 10.0 |
| | Lactose Ph.Eur | 488.5 |
| | Magnesium stearate | 1.5 |

*polyethylene glycol having a molecular weight of 400
**see above definition

The above formulations may be obtained by conventional procedures well known in the pharmaceutical art. The tablets may be enteric coated by conventional means, for example to provide a coating of cellulose acetate phthalate.

formula

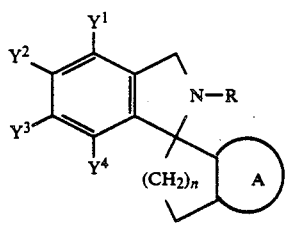

I

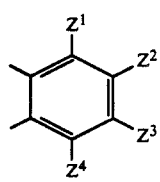

Ia

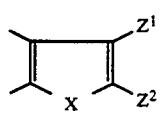

Ib

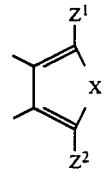

Ic

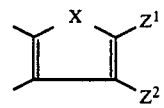

Id

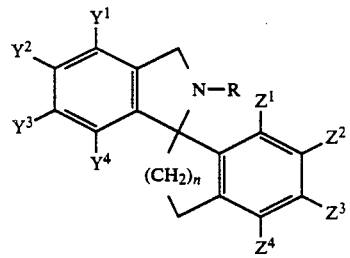

Ie

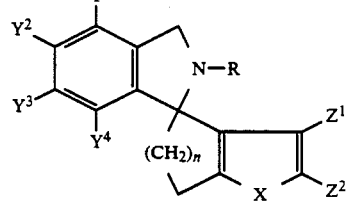

If

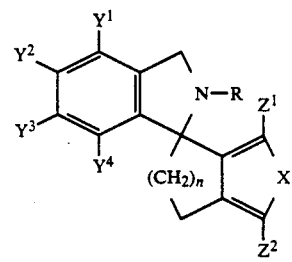

Ig

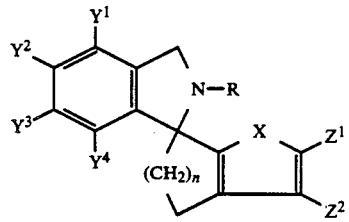

Ih

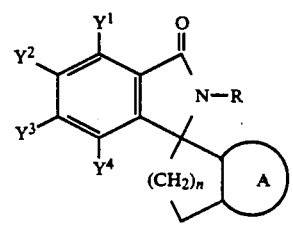

II

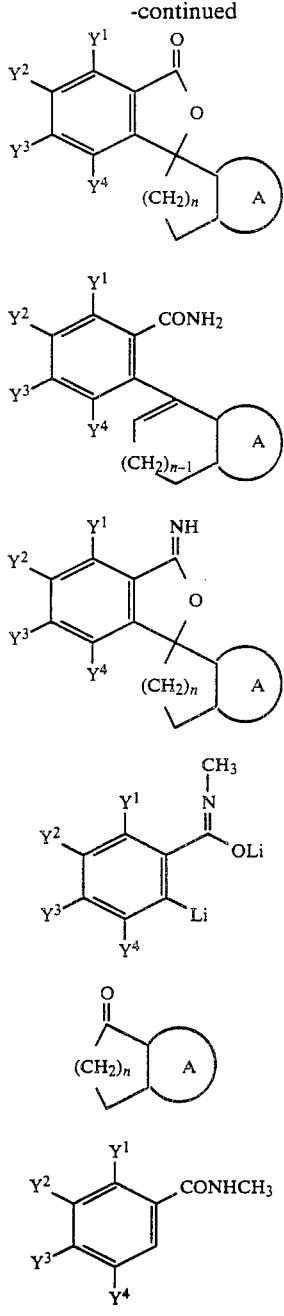
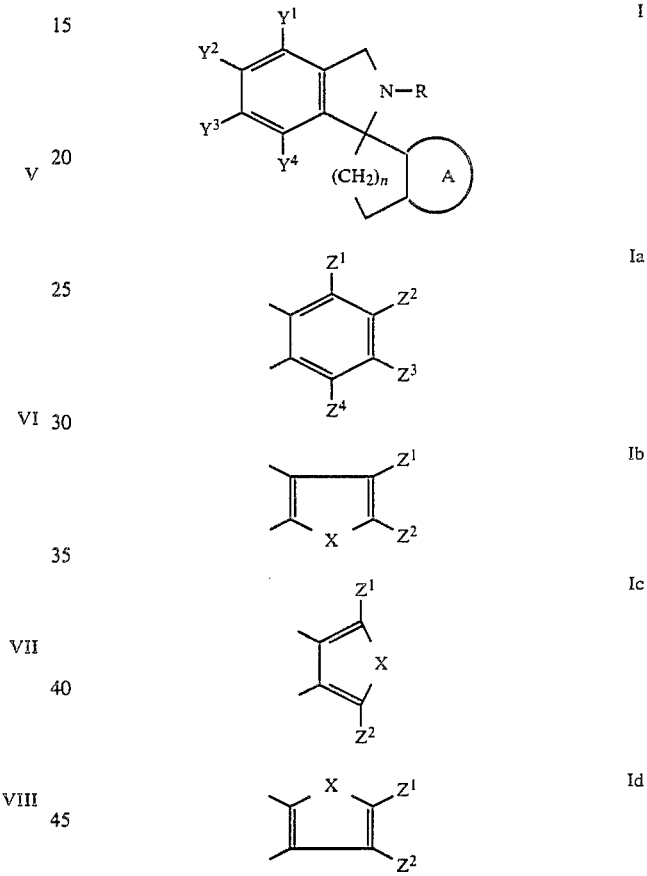

formulae, X is selected from a group consisting of O, S and N—$R^1$, wherein $R^1$ has the meaning given above for R, and $Z^1$, $Z^2$, $Z^3$ and $Z^4$ are independently selected from hydrogen, hydroxy, halo, (1-5C)alkyl, (1-5C)alkoxy, and trifluoromethyl, provided that not more than two or $Z^1$, $Z^2$, $Z^3$ and $Z^4$ are other than hydrogen, n is 1, 2, 3, or 4;

or a pharmaceutically acceptable salt thereof; provided that, when each of $Y^1$, $Y^2$, $Y^3$, and $Y^4$ is H, ring A is of formula Ia, each of $Z^1$, $Z^2$, $Z^3$, and $Z^4$ is H, and n=1, R is not H

What is claimed is:

1. A compound of formula I, formula set out hereinbelow, wherein:
   R is selected from a group consisting of hydrogen, benzyl, and (1-5C)alkyl optionally containing a double or triple bond provided that, if a double or triple bond is present, at least one methylene group intervenes between said double or triple bond and the nitrogen atom to which said alkyl is attached,
   $Y^1$, $Y^2$, $Y^3$ and $Y^4$ are independently selected from a group consisting of hydrogen, hydroxy, halo, (1-5-C)alkyl, (1-5C)alkoxy, and trifluoromethyl, provided that not more than two of $Y^1$, $Y^2$, $Y^3$ and $Y^4$ are other than hydrogen,
   ring A is selected from a group consisting of the members shown as formulae Ia, Ib, Ic, and Id, formulae set out hereinbelow, wherein, in said 2. A compound as claimed in claim 1 wherein:
   R is selected from a group consisting of hydrogen, benzyl, methyl, ethyl, propyl, isopropyl, butyl, sec-butyl, t-butyl, isobutyl, pentyl, isopentyl, allyl and propargyl;
   $R^1$, when present, is selected from a group consisting of hydrogen, benzyl, methyl, ethyl, propyl, isopropl, butyl, sec-butyl, t-butyl, isobutyl, pentyl, and isopentyl;
   $Y^1$, $Y^2$, $Y^3$ and $Y^4$ are independently selected from a group consisting of hydrogen, hydroxy, fluoro, chloro, trifluoromethyl, methyl, ethyl, propyl, isopropyl, butyl, sec-butyl, t-butyl, isobutyl, pentyl isopentyl, methoxy, ethoxy, propoxy, isopropoxy, butoxy, sec-butoxy, isobutoxy, t-butoxy, pentoxy and isopentoxy; and
   $Z^1$, $Z^2$, $Z^3$, and $Z^4$ are independently selected from hydrogen, hydroxy, fluoro, chloro, methyl, ethyl, propyl, isopropyl, butyl, sec-butyl, t-butyl, isobutyl, pentyl, isopentyl, methoxy, ethoxy, propoxy, isopropoxy, butoxy, sec-butoxy, isobutoxy, t-butoxy, pentoxy and isopentoxy.

3. A compound as claimed in claim 2 wherein:

R is selected from a group consisting of hydrogen, methyl, ethyl, propyl, and butyl;

$Y^1$, $Y^2$, $Y^3$ and $Y^4$ are independently selected from hydrogen, hydroxy, methyl, ethyl, propyl, methoxy, ethoxy, and propoxy;

$Z^1$, $Z^2$, $Z^3$, and $Z^4$ are independently selected from hydrogen, hydroxy, methyl, ethyl, propyl, methoxy, ethoxy, and propoxy;

$R^1$, when present, is selected from methyl, ethyl, and propyl; and n is 1, 2 or 3.

4. A compound as claimed in claim 3 wherein ring A has formula Ia or Ib.

5. A compound as claimed in claim 4 wherein:

R is selected from hydrogen, methyl, ethyl, and propyl;

$Y^1$, $Y^2$, $Y^3$ and $Y^4$ are independently selected from hydrogen, hydroxy, methoxy, and ethoxy;

$Z^1$, $Z^2$, $Z^3$, and $Z^4$ are independently selected from hydrogen, hydroxy, methoxy, and ethoxy; and X is S.

6. A compound as claimed in claim 5 which is 2'-methylspiro[4,5,6,7-tetrahydrobenzothiophene-4,1'-(1,3-dihydroisoindole)].

7. A pharmaceutical composition comprising a compound of formula I, formula set out hereinbelow, or a pharmaceutically acceptable salt thereof, wherein:

R is selected from a group consisting of hydrogen, benzyl, and (1-5C)alkyl optionally containing a double or triple bond provided that, if a double or triple bond is present, at least one methylene group intervenes between said double or triple bond and the nitrogen atom to which said alkyl is attached, $Y^1$, $Y^2$, $Y^3$ and $Y^4$ are independently selected from a group consisting of hydrogen, hydroxy, halo, (1-5C)alkyl, (1-5C)alkoxy, and trifluoromethyl, provided that not more than two of $Y^1$, $Y^2$, $Y^3$ and $Y^4$ are other than hydrogen, ring A is selected from a group consisting of the members shown as formulae Ia, Ib, Ic, and Id, formulae set out hereinbelow, wherein, in said formulae, X is selected from a group consisting of O, S and N—$R^1$, wherein $R^1$ has the meaning given above for R, and $Z^1$, $Z^2$, $Z^3$ and $Z^4$ are independently selected from hydrogen, hydroxy, halo, (1-5C)alkyl, (1-5C)alkoxy, and trifluoromethyl, provided that not more than two of $Z^1$, $Z^2$, $Z^3$ and $Z^4$ are other than hydrogen, n is 1, 2, 3, or 4;

and a pharmaceutically acceptable diluent or carrier

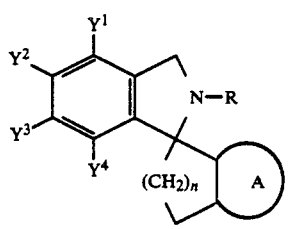

I

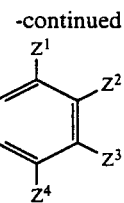

Ia

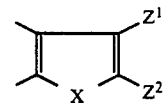

Ib

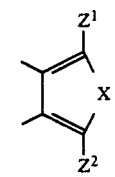

Ic

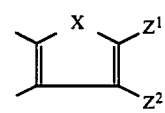

Id

8. A composition as claimed in claim 7 wherein:

R is selected from a group consisting of hydrogen, benzyl, methyl, ethyl, propyl, isopropyl, butyl, sec-butyl, t-butyl, isobutyl, pentyl, isopentyl, allyl and propargyl;

R1, when present, is selected from a group consisting of hydrogen, benzyl, methyl, ethyl, propyl, isopropyl, butyl, sec-butyl, t-butyl, isobutyl, pentyl, and isopentyl;

$Y^1$, $Y^2$, $Y^3$ and $Y^4$ are independently selected from a group consisting of hydrogen, hydroxy, fluoro, chloro, trifluoromethyl, methyl, ethyl, propyl, isopropyl, butyl, sec-butyl, t-butyl, isobutyl, pentyl isopentyl, methoxy, ethoxy, propoxy, isopropoxy, butoxy, sec-butoxy, isobutoxy, t-butoxy, pentoxy and isopentoxy; and $Z^1$, $Z^2$, $Z^3$, and $Z^4$ are independently selected from hydrogen, hydroxy, fluoro, chloro, methyl, ethyl, propyl, isopropyl, butyl, sec-butyl, t-butyl, isobutyl, pentyl, isopentyl, methoxy, ethoxy, propoxy, isopropoxy, butoxy, sec-butoxy, isobutoxy, t-butoxy, pentoxy and isopentoxy.

9. A composition as claimed in claim 8 wherein:

R is selected from a group consisting of hydrogen, methyl, ethyl, propyl, and butyl;

$Y^1$, $Y^2$, $Y^3$ and $Y^4$ are independently selected from hydrogen, hydroxy, methyl, ethyl, propyl, methoxy, ethoxy, and propoxy;

$Z^1$, $Z^2$, $Z^3$, and $Z^4$ are independently selected from hydrogen, hydroxy, methyl, ethyl, propyl, methoxy, ethoxy, and propoxy;

$R^1$, when present, is selected from methyl, ethyl, and propyl; and n is 1, 2 or 3.

10. A composition as claimed in claim 9 wherein ring A has formula Ia or Ib.

11. A composition as claimed in claim 10 wherein:

R is selected from hydrogen, methyl, ethyl, and propyl;

$Y^1$, $Y^2$, $Y^3$ and $Y^4$ are independently selected from hydrogen, hydroxy, methoxy, and ethoxy;

$Z^1$, $Z^2$, $Z^3$, and $Z^4$ independently are selected from hydrogen, hydroxy, methoxy, and ethoxy; and X is S.

12. A composition as claimed in claim 11 wherein said compound is 2'-methylspiro[4,5,6,7-tetrahydrobenzothiophene-4,1'-(1,3-dihydroisoindole)].

13. A method of treating neurological disorders, comprising administering to a mammal in need of such treatment a compound of formula I, formula set out hereinbelow, or a pharmaceutically acceptable salt thereof, wherein:

R is selected from a group consisting of hydrogen, benzyl, and (1-5C)alkyl optionally containing a double or triple bond provided that, if a double or triple bond is present, at least one methylene group intervenes between said double or triple bond and the nitrogen atom to which said alkyl is attached, $Y^1$, $Y^2$, $Y^3$ and $Y^4$ are independently selected from a group consisting of hydrogen, hydroxy, halo, (1-5C)alkyl, (1-5C)alkoxy, and trifluoromethyl, provided that not more than two of $Y^1$, $Y^2$, $Y^3$ and $Y^4$ are other than hydrogen, ring A is selected from a group consisting of the members shown as formulae Ia, Ib, Ic, and Id, formulae set out hereinbelow, wherein, in said formulae, X is selected from a group consisting of O, S and N—$R^1$, wherein $R^1$ has the meaning given above for R, and $Z^1$, $Z^2$, $Z^3$ and $Z^4$ are independently selected from hydrogen, hydroxy, halo, (1-5C)alkyl, (1-5C)alkoxy, and trifluoromethyl, provided that not more than two of $Z^1$, $Z^2$, $Z^3$ and $Z^4$ are other than hydrogen, n is 1, 2, 3, or 4

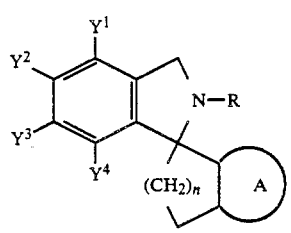

I

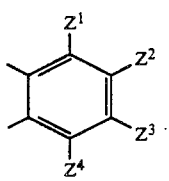

Ia

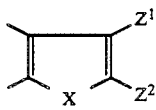

Ib

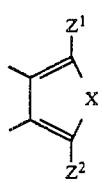

Ic

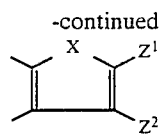

Id

14. A method as claimed in claim 13 wherein:
R is selected from a group consisting of hydrogen, benzyl, methyl, ethyl, propyl, isopropyl, butyl, sec-butyl, t-butyl, isobutyl, pentyl, isopentyl, allyl and propargyl;
$R^1$, when present, is selected from a group consisting of hydrogen, benzyl, methyl, ethyl, propyl, isopropyl, butyl, sec-butyl, t-butyl, isobutyl, pentyl, and isopentyl;
$Y^1$, $Y^2$, $Y^3$ and $Y^4$ are independently selected from a group consisting of hydrogen, hydroxy, fluoro, chloro, trifluoromethyl, methyl, ethyl, propyl, isopropyl, butyl, sec-butyl, t-butyl, isobutyl, pentyl isopentyl, methoxy, ethoxy, propoxy, isopropoxy, butoxy, sec-butoxy, isobutoxy, t-butoxy, pentoxy and isopentoxy; and
$Z^1$, $Z^2$, $Z^3$, and $Z^4$ are independently selected from hydrogen, hydroxy, fluoro, chloro, methyl, ethyl, propyl, isopropyl, butyl, sec-butyl, t-butyl, isobutyl, pentyl, isopentyl, methoxy, ethoxy, propoxy, isopropoxy, butoxy, sec-butoxy, isobutoxy, t-butoxy, pentoxy and isopentoxy.

15. A method as claimed in claim 14 wherein:
R is selected from a group consisting of hydrogen, methyl, ethyl, propyl, and butyl;
$Y^1$, $Y^2$, $Y^3$ and $Y^4$ are independently selected from hydrogen, hydroxy, methyl, ethyl, propyl, methoxy, ethoxy, and propoxy;
$Z^1$, $Z^2$, $Z^3$, and $Z^4$ are independently selected from hydrogen, hydroxy, methyl, ethyl, propyl, methoxy, ethoxy, and propoxy;
$R^1$, when present, is selected from methyl, ethyl, and propyl; and
n is 1, 2 or 3.

16. A method as claimed in claim 15 wherein ring A has formula Ia or Ib.

17. A method as claimed in claim 16 wherein:
R is selected from hydrogen, methyl, ethyl, and propyl;
$Y^1$, $Y^2$, $Y^3$ and $Y^4$ are independently selected from hydrogen, hydroxy, methoxy, and ethoxy;
$Z^1$, $Z^2$, $Z^3$, and $Z^4$ are independently selected from hydrogen, hydroxy, methoxy, and ethoxy; and
X is S.

18. A method as claimed in claim 17 wherein said compound is 2'-methylspiro[4,5,6,7-tetrahydrobenzothiophene-4,1'-(1,3-dihydroisoindole)].

19. A method as claimed in claim 13, wherein said mammal is man.

20. A method as claimed in claim 13, wherein said neurological disorder is stroke.

21. A compound of formula II set out hereinbelow wherein R, $Y^1$-$Y^4$, n, and ring A have any of the meanings defined in claim 1

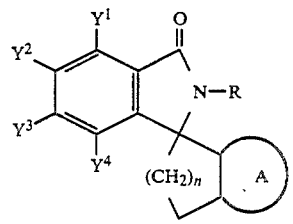

II

* * * * *